(12) United States Patent
Horn et al.

(10) Patent No.: US 11,673,859 B2
(45) Date of Patent: Jun. 13, 2023

(54) POLYMORPHIC FORMS OF N-(4-((4-(3-PHENYLUREIDO)PHENYL)SULFONYL)PHENYL)BENZOLSULFONAMIDE

(71) Applicant: KOEHLER PAPER SE, Oberkirch (DE)

(72) Inventors: Michael Horn, Offenburg (DE); Timo Stalling, Appenweier (DE); Christian Schnick, Merzhausen (DE)

(73) Assignee: KOEHLER PAPER SE, Oberkirch (DE)

( * ) Notice: Subject to any disclaimer, the term of this patent is extended or adjusted under 35 U.S.C. 154(b) by 0 days.

(21) Appl. No.: 17/779,947

(22) PCT Filed: Nov. 30, 2020

(86) PCT No.: PCT/EP2020/083901
§ 371 (c)(1),
(2) Date: May 25, 2022

(87) PCT Pub. No.: WO2021/105499
PCT Pub. Date: Jun. 3, 2021

(65) Prior Publication Data
US 2022/0363629 A1 Nov. 17, 2022

(30) Foreign Application Priority Data
Nov. 28, 2019 (DE) .................... 10 2019 132 401.7

(51) Int. Cl.
*C07C 317/42* (2006.01)
*B41M 5/333* (2006.01)

(52) U.S. Cl.
CPC ......... *C07C 317/42* (2013.01); *B41M 5/3336* (2013.01); *C07B 2200/13* (2013.01)

(58) Field of Classification Search
None
See application file for complete search history.

(56) References Cited

U.S. PATENT DOCUMENTS

2020/0039271 A1* 2/2020 Boxhammer .......... B41M 5/323
2022/0041923 A1 2/2022 Horn et al.

FOREIGN PATENT DOCUMENTS

DE 102018133168 A1 6/2020
EP 2923851 A1 9/2015
(Continued)

OTHER PUBLICATIONS

English Translation for International Preliminary Report on Patentability for Application No. PCT/EP2020/083901, dated May 17, 2022, 2 pages.

(Continued)

*Primary Examiner* — Sudhakar Katakam
*Assistant Examiner* — Jennifer C Sawyer
(74) *Attorney, Agent, or Firm* — Lippes Mathias LLP

(57) ABSTRACT

The present invention relates to an N-(4-((4-(3-phenylureido)phenyl)sulfonyl)phenyl)benzenesulfonamide in the polymorphic form $\omega^{18.9}$, characterised by an x-ray powder diffractogram having the Bragg angles (2θ/CuK$_\alpha$) 10.9, 11.7, 14.6, 15.0, 15.8, 16.6, 17.6, 18.9, 19.4, 20.9, 21.2, 22.0, 23.3, 24.4, 24.7, 26.1, 27.4, 29.4, 34.2, or in the polymorphic form $\alpha^{21.2}$, characterised by an x-ray powder diffractogram having the Bragg angles (2θ/CuK$_\alpha$) 8.7, 9.8, 10.8, 13.2, 13.9, 14.9, 15.2, 16.0, 17.4, 17.7, 18.7, 20.4, 21.2, 21.6, 22.3, 23.0, 23.3, 23.9, 24.4, 25.0, 25.8, 26.6, 28.1, 28.9, 29.4, 30.1, 30.6, 31.8, 34.5, 35.3, 35.6, 36.9, a method for production thereof, use thereof as a colour developer in a heat-sensitive recording material, and a heat-sensitive recording material comprising N-(4-((4-(3-phenylureido)phenyl)sulfonyl)phenyl)benzenesulfonamide in the polymorphic form $\omega^{18.9}$ or in the polymorphic form $\alpha^{21.2}$.

17 Claims, 1 Drawing Sheet

(56) References Cited

FOREIGN PATENT DOCUMENTS

| EP | 3263553 A1 | 3/2018 |
|---|---|---|
| JP | 3991857 B2 | 10/2007 |
| WO | 03101943 A1 | 12/2003 |
| WO | 2020127675 A1 | 6/2020 |

OTHER PUBLICATIONS

English Translation for Written Opinion for Application No. PCT/EP2020/083901, dated Mar. 9, 2021, 5 pages.
International Search Report for PCT/EP2020/083901, dated Mar. 9, 2021, 3 pages.
Written Opinion for PCT/EP2020/083901, dated Mar. 30, 2020, 6 pages.

\* cited by examiner

Fig 1: $\omega^{18,9}$–Form
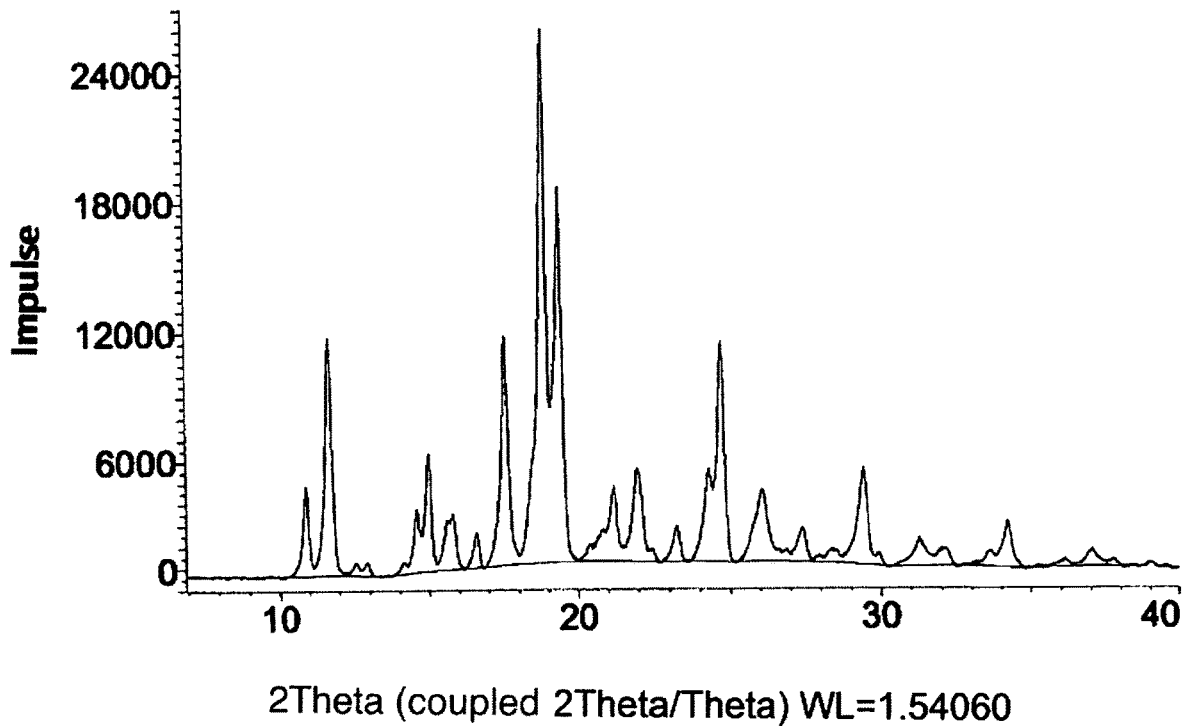
2Theta (coupled 2Theta/Theta) WL=1.54060
Fig 2: $\alpha^{21,2}$–Form
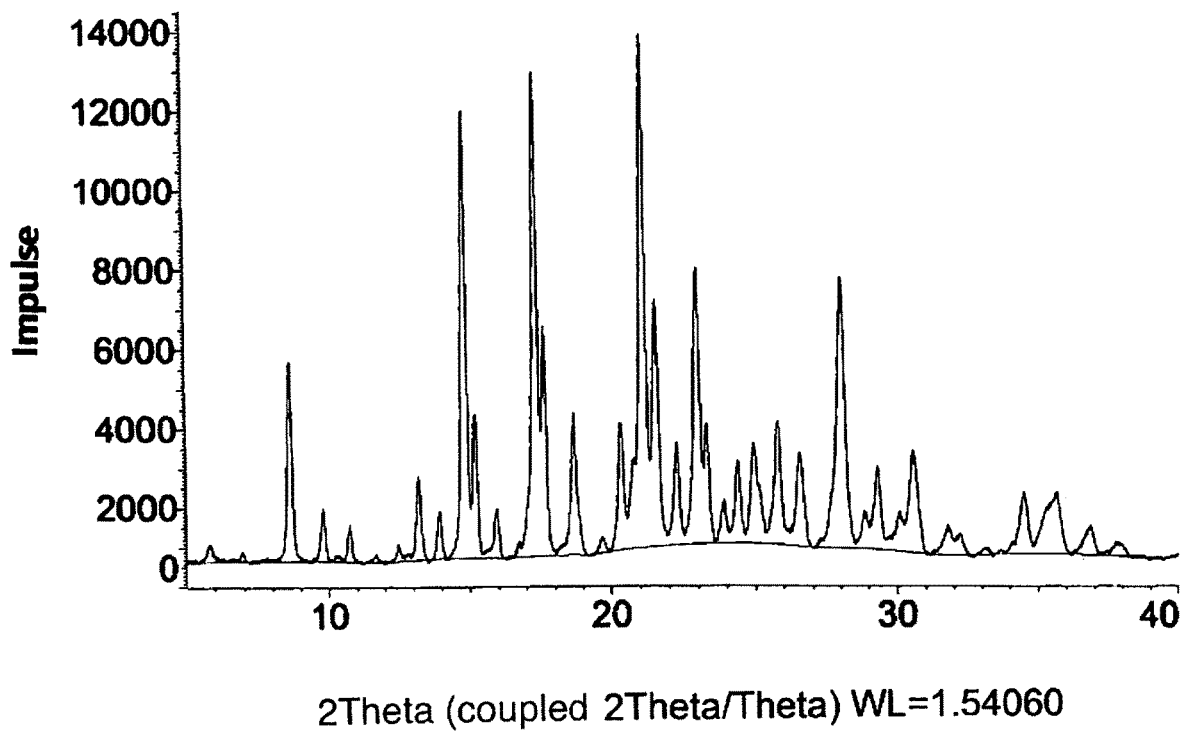
2Theta (coupled 2Theta/Theta) WL=1.54060

POLYMORPHIC FORMS OF N-(4-((4-(3-PHENYLUREIDO)PHENYL)SULFONYL)PHENYL)BENZOLSULFONAMIDE

The invention relates to polymorphic forms of N-(4-((4-(3-phenylureido)phenyl)sulfonyl)phenyl)benzenesulfonamide, a method for producing same, use thereof as colour developers in heat-sensitive recording materials, heat-sensitive recording materials comprising the polymorphic forms of N-(4-((4-(3-phenylureido)phenyl)sulfonyl)phenyl)benzenesulfonamide, and a method for producing such heat-sensitive recording materials.

Heat-sensitive recording materials for direct thermal printing applications which have a heat-sensitive colour-forming layer (thermal reaction layer) applied to a carrier substrate have been known for a long time. The heat-sensitive colour-forming layer usually contains a colour former and a colour developer, which react with each other under the influence of heat and thus lead to colour development.

DE102018133168 describes a heat-sensitive recording material comprising a carrier substrate and a heat-sensitive colour-forming layer containing at least one colour former and at least one phenol-free colour developer, and also the use of the phenol-free colour developer contained in the heat-sensitive recording material, wherein one of the disclosed colour developers is N-(4-((4-(3-phenylureido)phenyl)sulfonyl)phenyl)benzenesulfonamide, illustrated by formula (1),

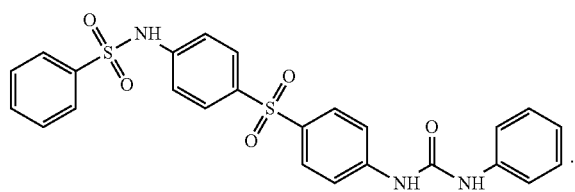

(1)

Although the crystalline compound (1) described in DE102018133168 has helpful properties in respect of its use as a colour developer in heat-sensitive recording materials, there is a need to determine and remedy any potential fluctuations in some application-related properties of the heat-sensitive recording materials produced using the compound (1), which fluctuations are generally related to changes in the purification conditions during the synthesis or during the course of optimisation of the synthesis of the compound (1) and cannot be explained by fluctuating degrees of purity of compound (1). This is of great importance especially against the background of the use of the compound (1) as a colour developer for producing heat-sensitive recording materials on an industrial scale, since making sure that the used raw materials adhere to specifications represents a major requirement and has to be ensured by the production process for the colour developer.

The heat-sensitive recording materials produced in accordance with DE102018133168 are characterised by the balance of important application-related properties. Irrespective of this, it is desirable to improve individual properties without bringing about a detrimental effect.

Molecules of phenol-free colour developers, such as the compound (1), thanks to their diverse functional groups, have many options for intra- and intermolecular binding in the crystal, and these can lead to the occurrence of a wide variety of crystal structures (polymorphic modifications) in these crystalline compounds. A key aspect of the characterisation of such materials by their physico-chemical properties relates to the knowledge of the crystal structure landscape. This includes primarily the identification of polymorphic modifications and knowledge of their identity.

An aim of the present invention is therefore to provide new, monophase polymorphic forms and methods for producing same.

A further aim of the present invention is to identify and utilise optimisation potentials for the application-related properties of heat-sensitive recording materials obtained with different polymorphic forms as compared to the prior art.

Especially, a further aim of the present invention lies in providing crystalline forms of a colour developer and heat-sensitive recording materials containing same, which have a significantly lower static sensitivity (higher starting temperature of the colour-forming reaction) in comparison to the corresponding heat-sensitive recording materials of the prior art, without displaying alternative application-related disadvantages, especially without compromising the dynamic sensitivity (dynamic response sensitivity in the printing process).

Polymorphic forms of conventional phenol-free colour developers and use thereof in heat-sensitive recording materials are known.

WO03/101943 A1 discloses three polymorphic forms of the phenol-free colour developer Pergafast® 201 (BASF), production thereof, and conversion and use in heat-sensitive recording materials.

EP3263553 A1 discloses a new polymorphic form of the colour developer N-(2-(3-phenylureido)phenyl)benzenesulfonamide and use thereof in heat-sensitive recording materials.

JP3991857 B discloses polymorphic forms of n-butyl 4-(3-(p-toluenesulfonyl)ureido)benzoate and advantageous use thereof as colour developer in heat-sensitive recording materials.

BRIEF DESCRIPTION OF THE DRAWINGS

FIG. 1 is an x-ray powder diffractogram taken from Example 2; and

FIG. 2 is an x-ray powder diffractogram taken from Example 3.

The inventors have succeeded in providing from the compound N-(4-((4-(3-phenylureido)phenyl)sulfonyl)phenyl)benzenesulfonamide (1) described in DE102018133168 the polymorphic form $\omega^{18.9}$, characterised by an x-ray powder diffractogram having the Bragg angles ($2\theta/CuK_\alpha$): 10.9, 11.7, 14.6, 15.0, 15.8, 16.6, 17.6, 18.9, 19.4, 20.9, 21.2, 22.0, 23.3, 24.4, 24.7, 26.1, 27.4, 29.4, 34.2 and the polymorphic form $\alpha^{21.2}$, characterised by an x-ray powder diffractogram having the Bragg angles ($2\theta/CuK_\alpha$): 8.7, 9.8, 10.8, 13.2, 13.9, 14.9, 15.2, 16.0, 17.4, 17.7, 18.7, 20.4, 21.2, 21.6, 22.3, 23.0, 23.3, 23.9, 24.4, 25.0, 25.8, 26.6, 28.1, 28.9, 29.4, 30.1, 30.6, 31.8, 34.5, 35.3, 35.6, 36.9.

In the crystal forms referred to as $\omega^{18.9}$ and $\alpha^{21.2}$, the superscript number refers to the most intense main peak in the x-ray powder diffractogram.

These new polymorphic forms are also characterised by their melting ranges and their IR absorption bands according to the following Table 1.

Table 1 summarises the most important measurement data for the polymorphic forms according to the invention of N-(4-((4-(3-phenylureido)phenyl)sulfonyl)phenyl)benzenesulfonamide, insofar as they relate to reflections from the P-XRD diffractograms, characteristic FTIR bands and the melt behaviour (DSC).

TABLE 1

| Poly-morph | 2 θ values of the most intense XRD peaks[#] | Melting range (° C.), Onset (DSC)[~] | Characteristic IR bands (cm$^{-1}$)[*] |
|---|---|---|---|
| $\omega^{18.9}$ | 10.9, 11.7, 14.6, 15.0, 15.8, 16.6, 17.6, <u>18.9</u>, 19.4, 20.9, 21.2, 22.0, 23.3, 24.4, 24.7, 26.1, 27.4, 29.4, 34.2 | 232-233 | 1092 (m), 1105 (i), 1145 (i); 1233 (i); 1319 (i); 1495 (i); 1548 (i); 1598 (i); 1655 (i); 3239 (m) |
| $a^{21.2}$ | 8.7, 9.8, 10.8, 13.2, 13.9, <u>14.9</u>, 15.2, 16.0, <u>17.4</u>, 17.7, 18.7, 20.4, <u>21.2</u>, 21.6, 22.3, 23.0, 23.3, 23.9, 24.4, 25.0, 25.8, 26.6, 28.1, 28.9, 29.4, 30.1, 30.6, 31.8, 34.5, 35.3, 35.6, 36.9 | 219-221 | 1089 (m); 1110 (m); 1149 (i); 1237 (m); 1311 (i); 1321 (i); 1500 (i); 1556 (i); 1597 (i); 1697 (i); 3365 (m); 3408 (m) |

[#]XRD, Broker D2 Phaser; selection from 2 θ values with rel. intensity ($I_{Peak}/I_{Main\ peak}$) ≥ 10%; main peak underlined.
[~]Netsch DSC 200 F3 Maia ® device, Al crucible with cold-welded, closed lid, heating rate 10 K/min, 25° C.-350° C. under $N_2$ atmosphere.
[*]FTIR, KBr pellets; i = intense, m = mean.

These new polymorphic forms can be obtained in monophase form by adding non-monophase N-(4-((4-(3-phenylureido)phenyl)sulfonyl)phenyl)benzenesulfonamide, produced in accordance with Example 1, following recrystallisation from EtOAc/n-hexane ($\alpha^{21.2}$) and by suspension in a solvent for a period of about 1 to 20 hours at a temperature of about 0° C. to the boiling point of the solvent ($\omega^{18.9}$).

The solvent can be selected from the class of aromatic hydrocarbons, chlorinated aromatic hydrocarbons, aliphatic or alicyclic hydrocarbons, chlorinated hydrocarbons, dialkylacylamides, aliphatic esters, aliphatic ketones, alicyclic ketones, aliphatic ethers, cyclic ethers, aliphatic alcohols, alicyclic alcohols, alkylnitriles or mixtures thereof. Preferred are toluene, cyclohexane, chloroform, dichloromethane, carbon tetrachloride, chlorobenzene, dimethyl formamide, dimethylacetamide, ethyl acetate, acetone, butanone, cyclohexanone, diethylether, tetrahydrofuran, dioxane, 1,2-dimethoxyethane, nitromethane, methanol, ethanol, isopropanol, acetonitrile or mixtures thereof.

The $\alpha^{21.2}$ form can be obtained by recrystallisation from EtOAc/n-hexane from non-monophase N-(4-((4-(3-phenylureido)phenyl)sulfonyl)phenyl)benzenesulfonamide, produced in accordance with Example 1.

The $\omega^{18.9}$ form can be obtained by suspending the $\alpha^{21.2}$ form in an organic solvent, preferably ethyl acetate and heating to a temperature of about 0° C. to the boiling point of the solvent for preferably about 1 hour to 20 hours.

The $\omega^{18.9}$ form can be obtained by suspending the $\alpha^{21.2}$ form in ethyl acetate and refluxing the suspension for about 2 hours to 8 hours, preferably for about 6 hours.

The $\alpha^{21.2}$ form can in turn also be obtained by recrystallisation of the monophase $\omega^{18.9}$ form from acetonitrile.

The present invention also relates to N-(4-((4-(3-phenylureido)phenyl)sulfonyl)phenyl)benzenesulfonamide in the polymorphic form $\omega^{18.9}$, obtainable by the above-described methods.

The present invention also relates to N-(4-((4-(3-phenylureido)phenyl)sulfonyl)phenyl)benzenesulfonamide in the polymorphic form $\alpha^{21.2}$, obtainable by the above-described methods.

The present invention also relates to the use of N-(4-((4-(3-phenylureido)phenyl)sulfonyl)phenyl)benzenesulfonamide in the polymorphic form $\omega^{18.9}$ or in the polymorphic form $\alpha^{21.2}$, as described above or as obtainable by one of the above-described methods as colour developers in a heat-sensitive recording material.

The present invention additionally relates to a heat-sensitive recording material comprising a carrier substrate and a heat-sensitive colour-forming layer containing at least one colour former and a colour developer, wherein the colour developer comprises the monophase $\omega^{18.9}$ form of N-(4-((4-(3-phenylureido)phenyl)sulfonyl)phenyl)benzenesulfonamide, characterised by an x-ray powder diffractogram with the following Bragg angles ($2\theta/CuK_\alpha$): 10.9, 11.7, 14.6, 15.0, 15.8, 16.6, 17.6, 18.9, 19.4, 20.9, 21.2, 22.0, 23.3, 24.4, 24.7, 26.1, 27.4, 29.4, 34.2 (see FIG. 1) or the monophase $\alpha^{21.2}$ form of N-(4-((4-(3-phenylureido)phenyl)sulfonyl)phenyl)benzenesulfonamide, characterised by an x-ray powder diffractogram having the Bragg angles ($2\theta/CuK_\alpha$): 8.7, 9.8, 10.8, 13.2, 13.9, 14.9, 15.2, 16.0, 17.4, 17.7, 18.7, 20.4, 21.2, 21.6, 22.3, 23.0, 23.3, 23.9, 24.4, 25.0, 25.8, 26.6, 28.1, 28.9, 29.4, 30.1, 30.6, 31.8, 34.5, 35.3, 35.6, 36.9 (see FIG. 2), or mixtures thereof.

In a further preferred embodiment of the heat-sensitive recording material, the at least one colour developer comprises the individual above-described polymorphic forms or mixtures thereof, in each case in combination with at least one compound of formula (2)

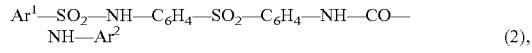

$$Ar^1—SO_2—NH—C_6H_4—SO_2—C_6H_4—NH—CO—NH—Ar^2 \quad (2),$$

wherein $Ar^1$ and $Ar^2$ are an unsubstituted or substituted phenyl group.

$Ar^1$ is preferably a phenyl group.
$Ar^2$ is preferably a phenyl group.
Especially preferably, $Ar^1$ is substituted with at least one $C_1$-$C_5$ alkyl group, an alkenyl group, an alkynyl group, a benzyl group, a formyl group, a CN group, a halogen group, an $NO_2$ group, an RO group, an R—CO— group, an $RO_2C$ group, an R—OCO group, an R—$SO_2O$ group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

$Ar^1$ is preferably substituted with at least one $C_1$-$C_5$ alkyl group, a halogen group, an RO group, an R—CO group or an $NO_2$ group, wherein R is a $C_1$-$C_5$ alkyl group.

$Ar^1$ is preferably substituted once.

Especially preferably, $Ar^2$ is substituted with at least one $C_1$-$C_5$ alkyl group, an alkenyl group, an alkynyl group, a benzyl group, a formyl group, a CN group, a halogen group, an $NO_2$ group, an RO group, an R—CO— group, an $RO_2C$ group, an R—OCO group, an R—$SO_2O$ group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

$Ar^2$ is preferably substituted with at least one $C_1$-$C_5$ alkyl group, a halogen group, an RO group, an R—CO group, an $RO_2C$ group or an $NO_2$ group, wherein R is a $C_1$-$C_5$ alkyl group.

$Ar^2$ is preferably substituted once.

$Ar^1$ and $Ar^2$ are substituted with at least one $C_1$-$C_5$ alkyl group, preferably in such a way that the $C_1$-$C_5$ alkyl group is a methyl group or butyl group, especially preferably a methyl group.

Ar$^1$ and Ar$^2$ are substituted with at least one halogen group preferably in such a way that the halogen group is a chloride group.

Ar$^1$ and Ar$^2$ are substituted with at least one RO group preferably in such a way that the RO group is a CH$_3$O group.

Ar$^1$ and Ar$^2$ are substituted with at least one R—CO group preferably in such a way that the R—CO group is a CH$_3$—CO group.

In an especially preferred embodiment, both Ar$^1$ and Ar$^2$ are a phenyl group. Such compounds are relatively easy and inexpensive to produce and deliver good results in respect of the properties described below.

In a preferred embodiment, the Ar$^1$—SO$_2$—NH group and the Ar$^2$—NH—CO—NH group are arranged in the 4 and 4' position or in the 3 and 3' position to the —C$_6$H$_4$—SO$_2$—C$_6$H$_4$ group. The arrangement is especially in the 4 and 4' position, since such compounds are relatively easy to produce and show good properties. Arrangement in the 4 and 4' position means that the Ar$^1$—SO—NH group and Ar$^2$—NH—CO—NH group are each arranged in the para position to the —C$_4$H$_4$—SO$_2$—C$_6$H$_4$ group. Correspondingly, the 3 and 3' position means an arrangement in the meta position.

The colour former according to the invention is preferably present in an amount of from about 3 to about 35% by weight, especially preferably in an amount of from about 10 to about 25% by weight, in relation to the total solids content of the heat-sensitive layer.

The selection of the carrier substrate is not critical. However, it is preferable to use paper, synthetic paper and/or a plastics film as the carrier substrate.

If necessary, there is at least one further intermediate layer between the carrier substrate and the heat-sensitive layer, with this intermediate layer having the task of improving the surface smoothness of the carrier for the heat-sensitive layer and providing a thermal barrier between the carrier paper and the heat-sensitive layer; organic hollow sphere pigments and/or calcined kaolins are preferably used in this intermediate layer.

At least one protective layer arranged above the heat-sensitive layer can also be provided in the heat-sensitive recording material according to the invention. Furthermore, the heat-sensitive recording material according to the invention can be equipped with a rear-side preparation. More specifically, this can be a self-adhesive layer or what is known as a "back-coat" layer for improving the rear-side printability or for minimising the curling of the heat-sensitive recording material under unfavourable humidity conditions. Magnetic/magnetisable coatings applied to the rear side are also contained within the scope of the rear-side preparations described here.

With regard to the choice of colour former, the present invention is also not subject to any major restrictions. However, the colour former is preferably a dye of the triphenylmethane, fluoran, azaphthalide and/or the fluorene type. A fluoran-type dye is a very especially preferred colour former, since its availability and balanced application properties make it possible to provide a recording material having an attractive price-performance ratio.

Especially preferred fluoran-type dyes are as follows:
3-diethylamino-6-methyl-7-anilinofluoran,
3-(N-ethyl-N-4-toludinamino)-6-methyl-7-anilinofluoran,
3-(N-ethyl-N-isoamylamino)-6-methyl-7-anilinofluoran,
3-diethylamino-6-methyl-7-(2,4-dimethylanilino)fluoran,
3-pyrrolidino-6-methyl-7-anilinofluoran,
3-(cyclohexyl-N-methylamino)-6-methyl-7-anilinofluoran,
3-diethylamino-7-(3-trifluoromethylanilino)fluoran,
3-N-n-dibutylamino-6-methyl-7-anilinofluoran,
3-diethylamino-6-methyl-7-(3-methylanilino)fluoran,
3-N-n-dibutylamino-7-(2-chloroanilino)fluoran,
3-(N-ethyl-N-tetrahydrofurfurylamino)-6-methyl-7-anilinofluoran,
3-(N-methyl-N-propylamino)-6-methyl-7-anilinofluoran,
3-(N-ethyl-N-ethoxypropylamino)-6-methyl-7-anilinofluoran,
3-(N-ethyl-N-isobutylamino)-6-methyl-7-anilinofluoran and/or
3-dipentylamino-6-methyl-7-anilinofluoran.

The colour formers can be used as single substances, but also as arbitrary mixtures of two or more colour formers, provided that the desirable application properties of the recording materials do not suffer as a result.

The colour former is preferably present in an amount of from about 5 to about 30% by weight, especially preferably in an amount of from about 8 to about 20% by weight, in relation to the total solids content of the heat-sensitive layer.

To control specific application-related properties, it can be advantageous if one or more further (bis)phenolic or non-phenolic colour developers are present additionally to the previously disclosed application forms of the colour developer in the heat-sensitive colour-forming layer.

In addition to the at least one colour former and the at least one colour developer, the heat-sensitive colour-forming layer can contain one or more sensitising agents, also known as thermal solvents or melting aids, which has the advantage that it is easier to control thermal print sensitivity.

In general, crystalline substances with a melting point between about 90 and about 150° C. are advantageously used as sensitising agents, and, in the molten state, dissolve the colour-forming components (colour former and colour developer) without disturbing the formation of the colour complex.

Preferably, the sensitising agent is a fatty acid amide, such as stearamide, beheneamide or palmitamide, an ethylene-bis-fatty acid amide, such as N,N-ethylene-bis-stearic acid amide or N,N-ethylene-bis-oleic acid amide, a fatty acid alkanolamide, such as N-(hydroxymethyl)stearamide, N-hydroxymethylpalmitamide or hydroxyethylstearamide, a wax, such as polyethylene wax or montan wax, a carboxylic acid ester, such as dimethyl terephthalate, dibenzyl terephthalate, benzyl-4-benzyloxybenzoate di-(4-methylbenzyl) oxalate, di-(4-chlorobenzyl)oxalate or di-(4-benzyl)oxalate, ketones such as 4-acetylbiphenyl, an aromatic ether such as 1,2-diphenoxy-ethane, 1,2-di(3-methylphenoxy)ethane, 2-benzyloxynaphthalene, 1,2-bis(phenoxymethyl)benzene or 1,4-diethoxynaphthalene, an aromatic sulfone, such as diphenylsulfone, and/or an aromatic sulfonamide, such as 4-toluenesulfonamide, benzenesulfonanilide or N-benzyl-4-toluenesulfonamide, or aromatic hydrocarbons, such as 4-benzylbiphenyl.

In addition to the colour former, the phenol-free colour developer and the sensitising agent, in a further preferred embodiment at least one stabiliser (anti-degradation agent) is optionally present in the heat-sensitive colour-forming layer.

The stabiliser is preferably constituted by sterically hindered phenols, especially preferably 1,1,3-tris-(2-methyl-4-hydroxy-5-cyclohexyl-phenyl)-butane, 1,1,3-tris-(2-methyl-4-hydroxy-5-tert-butylphenyl)-butane, 1,1-bis-(2-methyl-4-hydroxy-5-tert-butyl-phenyl)-butane.

Also urea-urethane compounds (commercial product UU) or ethers derived from 4,4'-dihydroxydiphenylsulfone, such as 4-benzyloxy-4'-(2-methylglycidyloxy)-diphenylsulfone (trade name NTZ-95®, Nippon Soda Co. Ltd.), or oligomeric ethers (trade name D90®, Nippon Soda Co. Ltd.) can be used as stabilisers in the recording material according to the invention.

The stabiliser is preferably present in an amount of 0.2 to 0.5 parts by weight, in relation to the at least one phenol-free colour developer of the compound of formula (I).

In a further preferred embodiment, the heat-sensitive colour-forming layer contains at least one binder. These are preferably water-soluble starches, starch derivatives, starch-based biolatices of the EcoSphere® type, methyl cellulose, hydroxyethyl cellulose, carboxymethyl celluloses, partially or completely saponified polyvinyl alcohols, chemically modified polyvinyl alcohols, or styrene-maleic anhydride copolymers, styrene-butadiene copolymers, acrylamide-(meth)acrylate copolymers, acrylamide-acrylate-methacrylate terpolymers, polyacrylates, poly(meth)acrylic acid esters, acrylate-butadiene copolymers, polyvinyl acetates and/or acrylonitrile-butadiene copolymers.

In a further preferred embodiment, at least one release agent (anti-stick agent) or lubricant is present in the heat-sensitive colour-forming layer. These agents are preferably fatty acid metal salts, such as zinc stearate or calcium stearate, or behenate salts, synthetic waxes, for example in the form of fatty acid amides, such as stearic acid amide and behenic acid amide, fatty acid alkanol amides, such as stearic acid methylolamide, paraffin waxes with different melting points, ester waxes of different molecular weights, ethylene waxes, propylene waxes of different hardnesses and/or natural waxes, such as carnauba wax or montan wax.

In a further preferred embodiment, the heat-sensitive colour-forming layer contains pigments. One of the advantages of using these pigments is that they can fix on their surface the molten chemicals produced in the thermal printing process. Pigments can also be used to control the surface whiteness and opacity of the heat-sensitive colour-forming layer and its printability with conventional inks. Lastly, pigments have an "extender function", for example for the relatively expensive colouring functional chemicals.

Especially suitable pigments are inorganic pigments, both synthetic and natural, preferably clays, precipitated or natural calcium carbonates, aluminium oxides, aluminium hydroxides, silicas, precipitated and pyrogenic silicas (for example Aerodisp® types), diatomaceous earths, magnesium carbonates, talc, kaolin, but also organic pigments, such as hollow pigments with a styrene/acrylate copolymer wall or urea/formaldehyde condensation polymers. These can be used alone or in any mixture.

To control the surface whiteness of the heat-sensitive recording material according to the invention, optical brighteners can be incorporated into the heat-sensitive colour-forming layer. These are preferably stilbenes.

In order to improve certain coating properties, it is preferable in individual cases to add further components, especially rheological auxiliaries such as thickeners and/or surfactants, to the mandatory components of the heat-sensitive recording material according to the invention.

The applied weight per unit area of the (dry) heat-sensitive layer is preferably about 1 to about 10 g/m², preferably about 3 to about 6 g/m².

In an especially preferred embodiment, the heat-sensitive recording material is one according to claim 8, in which a dye of the fluoran type is used as colour former and a sensitising agent, selected from the group consisting of fatty acid amides, aromatic sulfones, benzyloxalates and/or aromatic ethers, is additionally present. In this preferred embodiment it is also advantageous that about 1.5 to about 4 parts by weight of the phenol-free colour developer according to claim 1 are present in relation to the colour former.

The heat-sensitive recording material according to the invention can be obtained using known production methods.

However, it is preferable to obtain the recording material according to the invention by a method in which an aqueous suspension containing the starting materials of the heat-sensitive colour-forming layer is applied to a carrier substrate and dried, the aqueous application suspension having a solids content of from about 20 to about 75% by weight, preferably of from about 30 to about 50% by weight, and is applied and dried by the curtain coating process at an operating speed of the coating plant of at least about 400 m/min.

This process is especially advantageous from an economic point of view.

If the solids content falls below the value of about 20% by weight, the economic efficiency is reduced because a large amount of water must be removed from the coating by gentle drying in a short time, which has a negative effect on the coating speed. If, on the other hand, the value of 75% by weight is exceeded, then this only leads to an increased technical effort to ensure the stability of the coating colour curtain during the coating process.

In the curtain coating process, a free-falling curtain of a coating dispersion is formed. By free fall, the coating dispersion, which is in the form of a thin film (curtain), is "poured" onto a substrate to apply the coating dispersion to the substrate. Document DE 10 196 052 T1 discloses the use of the curtain coating process in the production of information recording materials, also including, amongst other things, heat-sensitive recording materials, wherein multi-layer recording layers are realised by applying the curtain, which consists of several coating dispersion films, to substrates (speed maximum 200 m/min).

Setting the operating speed of the coating plant to at least about 400 m/min has both economic and technical advantages. Preferably, the operating speed is at least about 750 m/min, especially preferably at least about 1000 m/min, and very especially preferably at least about 1500 m/min. It was especially surprising that, even at the latter speed, the heat-sensitive recording material obtained is not affected in any way, and the operation runs optimally even at this high speed.

In a preferred embodiment of the method according to the invention, the aqueous deaerated coating suspension has a viscosity of about 150 to about 800 mPas (Brookfield, 100 rpm, 20° C.). If the viscosity falls below the value of about 150 mPas or exceeds the value of about 800 mPas, this leads to poor runnability of the coating mass at the coating unit. The viscosity of the aqueous deaerated coating suspension is especially preferably about 200 to about 500 mPas.

In a preferred embodiment, the surface tension of the aqueous application suspension can be adjusted to about 25 to about 60 mN/m, preferably to about 35 to about 50 mN/m (measured according to the static ring method according to Du Noüy, DIN 53914), in order to optimise the process.

The heat sensitive colour-forming layer can be formed on-line or in a separate coating process off-line. This also applies to any subsequently applied layers or intermediate layers.

It is advantageous if the dried heat-sensitive colour-forming layer is subjected to a smoothing measure.

It is advantageous here to adjust the Bekk smoothness, measured according to ISO 5627:1995-03, to about 100 to about 1000 sec., preferably to about 250 to about 600 sec.

The surface roughness (PPS) according to ISO 8791-4: 2008-05 is in the range of about 0.50 to about 2.50 μm, especially preferably between 1.00 and 2.00 μm.

The invention is explained in detail below on the basis of non-limiting examples.

EXAMPLES

Example 1

The non-monophase compound N-(4-((4-(3-phenylureido)phenyl)sulfonyl)phenyl)benzenesulfonamide was produced as follows:

A solution of 7.5 mmol of phenylisocyanate in 20 ml dichloromethane was added dropwise at 0° C. with stirring to a mixture of 7.5 mmol of 4,4'-diaminodiphenylsulfone and 7.5 mmol pyridine in 80 mL dichloromethane. The reaction solution was stirred for 16 hours at room temperature. A solution of 7.5 mmol of benzenesulfonyl chloride in 15 ml dichloromethane was then added dropwise at 0° C. with stirring. The reaction mixture was refluxed and the progress of the reaction was monitored by means of HPLC. Once the reaction was complete, the product was filtered off, washed with dichloromethane, and dried in a vacuum.

Example 2

6.84 g of N-(4-((4-(3-phenylureido)phenyl)sulfonyl)phenyl)benzenesulfonamide, produced according to Example 1, was recrystallised from EtOAc/n-hexane. N-(4-((4-(3-phenylureido)phenyl)sulfonyl)phenyl)benzenesulfonamide was obtained, characterised by an x-ray powder diffractogram with the following Bragg angles ($2\theta$/CuK$_\alpha$): 8.7, 9.8, 10.8, 13.2, 13.9, 14.9, 15.2, 16.0, 17.4, 17.7, 18.7, 20.4, 21.2, 21.6, 22.3, 23.0, 23.3, 23.9, 24.4, 25.0, 25.8, 26.6, 28.1, 28.9, 29.4, 30.1, 30.6, 31.8, 34.5, 35.3, 35.6, 36.9 (see FIG. 2). This compound was suspended in 225 ml ethyl acetate and refluxed for six hours. After cooling, the solvent was removed and N-(4-((4-(3-phenylureido)phenyl)sulfonyl)phenyl)benzenesulfonamide was obtained, characterised by an x-ray powder diffractogram with the following Bragg angles ($2\theta$/CuK$_\alpha$): 10.9, 11.7, 14.6, 15.0, 15.8, 16.6, 17.6, 18.9, 19.4, 20.9, 21.2, 22.0, 23.3, 24.4, 24.7, 26.1, 27.4, 29.4, 34.2 (see FIG. 1).

Example 3

N-(4-((4-(3-phenylureido)phenyl)sulfonyl)phenyl)benzenesulfonamid, characterised by an x-ray powder diffractogram with the following Bragg angles ($2\theta$/CuK$_\alpha$): 10.9, 11.7, 14.6, 15.0, 15.8, 16.6, 17.6, 18.9, 19.4, 20.9, 21.2, 22.0, 23.3, 24.4, 24.7, 26.1, 27.4, 29.4, 34.2 (see FIG. 1) was recrystallised from acetonitrile. The obtained N-(4-((4-(3-phenylureido)phenyl)sulfonyl)phenyl)benzenesulfonamide was characterised by an x-ray powder diffractogram with the following Bragg angles ($2\theta$/CuK$_\alpha$): 8.7, 9.8, 10.8, 13.2, 13.9, 14.9, 15.2, 16.0, 17.4, 17.7, 18.7, 20.4, 21.2, 21.6, 22.3, 23.0, 23.3, 23.9, 24.4, 25.0, 25.8, 26.6, 28.1, 28.9, 29.4, 30.1, 30.6, 31.8, 34.5, 35.3, 35.6, 36.9 (see FIG. 2).

Example 4

A heat-sensitive recording material or thermal paper was produced, with the following formulations of aqueous application suspensions being used to form a composite structure on a carrier substrate, and then the other layers, especially a protective layer, being formed in the usual manner, which will not be discussed separately here.

An aqueous coating suspension was applied to one side of a 63 g/m$^2$ synthetic base paper (Yupo® FP680) using a doctor bar on a laboratory scale to form the heat-sensitive colour-forming layer of a heat-sensitive recording paper. After drying, a thermal recording sheet was obtained. The application rate of the heat-sensitive colour-forming layer was between 3.8 and 4.2 g/m$^2$.

Production of the dispersions (in each case for 1 part by weight) for the application suspensions:

The aqueous dispersion A (colour former dispersion) was produced by grinding 20 parts by weight of 3-N-n-dibutylamino-6-methyl-7-anilinofluoran (ODB-2) with 33 parts by weight of a 15% aqueous solution of Ghosenex™ L-3266 (sulfonated polyvinyl alcohol, Nippon Ghosei) in a bead mill.

The aqueous dispersion B (colour developer dispersion) was produced by grinding 40 parts by weight of the colour developer (N-(4-((4-(3-phenylureido)phenyl)sulfonyl)phenyl)benzenesulfonamide, form $\omega^{18,9}$ or form $\alpha^{21,2}$ together with 66 parts by weight of a 15% aqueous solution of Ghosenex™ L-3266 in a bead mill.

The aqueous dispersion C (sensitising dispersion) is produced by grinding 40 parts by weight of the sensitiser with 33 parts by weight of a 15% aqueous solution of Ghosenex™ L-3266 in a bead mill.

The following sensitising agents were used: 1,2-diphenoxyethane (DPE), stearamide (SA), diphenylsulfone (DPS), di-(4-methylbenzyl)oxalate (HS3520), benzyloxynaphthalene (BON), 1,2-di(3-methylphenoxy)ethane (EGTE).

All dispersions produced by grinding had an average particle size $D_{(4.3)}$ of 0.80 to 1.20 μm. The particle size distribution of the dispersions was measured by laser diffraction with a Coulter LS230 apparatus from Beckman Coulter.

Dispersion D (lubricant dispersion) is a 20% zinc stearate dispersion consisting of 9 parts by weight of Zn-stearate, 1 part by weight of Ghosenex™ L-3266, and 40 parts by weight of water.

Pigment P is a 72% coating kaolin suspension (Lustra® S, BASF).

The binder consists of a 10% aqueous polyvinyl alcohol solution (Mowiol 28-99, Kuraray Europe).

The heat-sensitive application suspension is produced by mixing, with stirring, 1 part of A, 1 part of B, 1 part of C, 56 parts of D, 146 parts of pigment P and 138 parts of binder solution (all parts by weight), taking into account the order of introduction B, D, C, P, A, binder, and bringing the mixture to a solids content of about 25% with water.

The heat-sensitive coating suspensions obtained in this way were used to produce composite structures consisting of paper carrier and thermal reaction layer.

The thermal recording materials were evaluated as described below (see Table 2).

(1) Dynamic Colour Density:

The papers (6 cm wide strips) were thermally printed with a chessboard pattern with 10 energy levels using an Atlantek 200 test printer (Atlantek, USA) with a Kyocera print bar of 200 dpi and 560 ohms at an applied voltage of 20.6 V and a maximum pulse width of 0.8 ms. The image density (optical density, o.d.) was measured with a SpectroEye densitometer from X-Rite at an energy level of 0.45 mJ/dot. In each case, the highest o.d. Value of the chessboard pattern was taken into consideration for the evaluation (Table 2). The measurement uncertainty of the o.d. values was estimated at ≤2%.

(2) Static Colour Density (Starting Temperature):

The recording sheet was pressed against a series of thermostatically controlled metallic stamps heated to different temperatures with a contact pressure of 0.2 kg/cm² and a contact time of 5 seconds (thermal tester TP 3000QM, Maschinenfabrik Hans Rychiger AG, Steffisburg, Switzerland). The image density (opt. density) of the images thus produced was measured with a SpectroEye densitometer from X-Rite.

The static starting point was, by definition, the lowest temperature in ° C. at which an optical density of 0.2 was achieved. The accuracy of the measuring method was ≤±0.5° C.

Table 2 summarises the evaluation of the recording materials produced.

TABLE 2

| Polymorphic form of the CD | Sensitising agent | o.d. max. | Starting point (° C.) |
|---|---|---|---|
| $\omega^{18.9}$ | EGTE | 1.29 | 93 |
| $a^{21.2}$ |  | 1.27 | 91 |
| $\omega^{18.9}$ | DPE | 1.30 | 85 |
| $a^{21.2}$ |  | 1.29 | 84 |
| $\omega^{18.9}$ | SA | 1.19 | 92 |
| $a^{21.2}$ |  | 1.18 | 89 |
| $\omega^{18.9}$ | BON | 1.24 | 91 |
| $a^{21.2}$ |  | 1.24 | 88 |
| $\omega^{18.9}$ | DPS | 1.22 | 91 |
| $a^{21.2}$ |  | 1.22 | 87 |
| $\omega^{18.9}$ | HS 3520 | 1.28 | 90 |
| $a^{21.2}$ |  | 1.27 | 89 |

It can be deduced from the above examples that the heat-sensitive recording material of the present invention shows the following advantageous properties especially:

(1) Both the use of the $\alpha^{21.2}$ form and the use of the $\omega^{18.9}$ form as colour developer lead to high maximum print densities of the heat-sensitive recording materials according to the invention and to high temperatures at which a visually discernible greying of the heat-sensitive recording materials according to the invention (starting point ° C.) occurs.

(2) The temperature from which a visually discernible greying of the recording materials according to the invention occurs (static starting point) is higher with use of the polymorph $\omega^{18.9}$ than in the examples with the $\alpha^{21.2}$ form of the colour developer. On the one hand, this gives rise to the possibility for use of the heat-sensitive recording materials manufactured with the $\omega^{18.9}$ form also at higher ambient temperatures, and on the other hand a thermally less sensitive coating benefits the process when drying the aqueous coating (Table 2).

(3) The recorded image of the heat-sensitive recording materials obtained with the $\omega^{18.9}$ form of the colour developer has practically the same maximum print density (optical density) as that of the $\alpha^{21.2}$ form (Table 2).

(4) Both the starting point and the print density generated dynamically during the printing process can be influenced to a significant extent by the sensitising agent. The data from Table 2 reveal that the advantageous properties according to (2) and (3) are valid for a representative selection of sensitising agents.

The invention claimed is:

1. An N-(4-((4-(3-phenylureido)phenyl)sulfonyl)phenyl) benzenesulfonamide in the polymorphic form $\omega^{18.9}$, characterised by an x-ray powder diffractogram having the Bragg angles (2θ/CuK$_\alpha$) 10.9, 11.7, 14.6, 15.0, 15.8, 16.6, 17.6, 18.9, 19.4, 20.9, 21.2, 22.0, 23.3, 24.4, 24.7, 26.1, 27.4, 29.4, 34.2, or in the polymorphic form $\alpha^{21.2}$, characterised by an x-ray powder diffractogram having the Bragg angles (2θ/CuK$_\alpha$) 8.7, 9.8, 10.8, 13.2, 13.9, 14.9, 15.2, 16.0, 17.4, 17.7, 18.7, 20.4, 21.2, 21.6, 22.3, 23.0, 23.3, 23.9, 24.4, 25.0, 25.8, 26.6, 28.1, 28.9, 29.4, 30.1, 30.6, 31.8, 34.5, 35.3, 35.6, 36.9.

2. The N-(4-((4-(3-phenylureido)phenyl)sulfonyl)phenyl) benzenesulfonamide in the polymorphic form $\omega^{18.9}$ or in the polymorphic form $\alpha^{21.2}$ according to claim 1, characterised in that the polymorphic form $\omega^{18.9}$ has characteristic absorption bands according to Fourier transformation infrared spectroscopy at the wavelengths 1092 cm$^{-1}$ 1105 cm$^{-1}$, 1145 cm$^{-1}$, 1233 cm$^{-1}$, 1319 cm$^{-1}$, 1495 cm$^{-1}$, 1548 cm$^{-1}$, 1598 cm$^{-1}$, 1655 cm$^{-1}$ and 3239 cm$^{-1}$ and the polymorphic form $\alpha^{21.2}$ has characteristic absorption bands according to Fourier transformation infrared spectroscopy at the wavelengths 1089 cm$^{-1}$, 1110 cm$^{-1}$, 1149 cm$^{-1}$, 1237 cm$^{-1}$, 1311 cm$^{-1}$, 1321 cm$^{-1}$, 1500 cm$^{-1}$, 1556 cm$^{-1}$, 1597 cm$^{-1}$, 1697 cm$^{-1}$, 3365 cm$^{-1}$ and 3408 cm$^{-1}$.

3. The N-(4-((4-(3-phenylureido)phenyl)sulfonyl)phenyl) benzenesulfonamide in the polymorphic form $\omega^{18.9}$ or in the polymorphic form $\alpha^{21.2}$ according to claim 1, characterised in that the polymorphic form $\omega^{18.9}$ has a melting range of 232 to 233° C. and the polymorphic form $\alpha^{21.2}$ has a melting range of 219 to 221° C.

4. A method for producing N-(4-((4-(3-phenylureido) phenyl)sulfonyl)phenyl)benzenesulfonamide in the polymorphic form $\omega^{18.9}$ according to claim 1, characterised in that monophase N-(4-((4-(3-phenylureido)phenyl)sulfonyl) phenyl) benzenesulfonamide in the polymorphic form $\alpha^{21.2}$ is heated.

5. A method for producing N-(4-((4-(3-phenylureido) phenyl)sulfonyl)phenyl) benzenesulfonamide in the polymorphous form $\alpha^{21.2}$, according to claim 1, characterised in that non-monophase N-(4-((4-(3-phenylureido)phenyl) sulfonyl)phenyl)benzenesulfonamide is obtained by recrystallisation from a mixture of ethyl acetate and n-hexane, or in that monophase N-(4-((4-(3-phenylureido)phenyl)sulfonyl)phenyl)benzenesulfonamide in the polymorphic form $\omega^{18.9}$ is recrystallised from acetonitrile.

6. A heat-sensitive recording material, comprising a carrier substrate and a heat-sensitive colour-forming layer containing at least one colour former and at least one phenol-free colour developer, wherein the at least one phenol-free colour developer is N-(4-((4-(3-phenylureido)phenyl)sulfonyl)phenyl)benzenesulfonamide in the polymorphic form $\omega^{18.9}$ and/or in the polymorphic form $\alpha 1^{21.2}$, according to claim 1.

7. The heat-sensitive recording material according to claim 6, wherein the colour developer is present in an amount of from about 3 to about 35% by weight in relation to the total solids content of the heat-sensitive layer.

8. The heat-sensitive recording material according to claim 6, wherein the at least one colour former is a dye of the triphenylmethane type, of the fluoran type, of the azaphthalide type and/or of the fluorene type.

9. The heat-sensitive recording material according to claim 6, wherein, besides the phenol-free colour developer, at least one colour developer of general formula

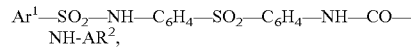

wherein Ar$^1$ and Ar$^2$ are an unsubstituted or substituted phenyl group, is also present.

10. The heat-sensitive recording material according to claim 9, characterised in that $Ar^1$ is a phenyl group, and/or in that $Ar^2$ is a phenyl group.

11. The heat-sensitive recording material according to claim 9, characterised in that $Ar^1$ is substituted with at least one $C_1$-$C_5$ alkyl group, an alkenyl group, an alkynyl group, a benzyl group, a formyl group, a CN group, a halogen group, an $NO_2$ group, an RO group, an R—CO group, an $RO_2C$ group, an R—OCO group, an R—$SO_2$O group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

12. A method for producing a heat-sensitive recording material according to claim 6, wherein an aqueous suspension containing the starting materials of the heat-sensitive colour-forming layer is applied to a carrier substrate and dried, wherein the aqueous application suspension has a solids content of from about 20 to about 75% by weight and is applied and dried by the curtain coating process at an operating speed of the coating plant of at least about 400 m/min.

13. The method of claim 4 wherein the monophase N-(4-((4-(3-phenylureido)phenyl)sulfonyl)phenyl) benzenesulfonamide in the polymorphic form $\alpha^{21.2}$ is refluxed in an organic solvent.

14. The method of claim 13 wherein the organic solvent is ethyl acetate.

15. The heat-sensitive recording material according to claim 6, wherein the colour developer is present in an amount of from about 10 to about 25% by weight in relation to the total solids content of the heat-sensitive layer.

16. The heat-sensitive recording material according to claim 6, wherein the at least one colour former is a dye of the fluoran type.

17. A method for producing a heat-sensitive recording material according to claim 6, wherein the aqueous application suspension has a solids content of from about 30 to about 50% by weight and is applied and dried by the curtain coating process at an operating speed of the coating plant of at least about 1000 m/min.

* * * * *